United States Patent
Amisar

(10) Patent No.: US 9,417,226 B2
(45) Date of Patent: Aug. 16, 2016

(54) REAGENT, METHOD AND KIT FOR THE DETECTION OF NITRO ALIPHATIC COMPOUNDS

(75) Inventor: Shai Amisar, Tel Aviv (IL)

(73) Assignee: MISTRAL DETECTION LTD, Herzliya Pituach (IL)

(*) Notice: Subject to any disclaimer, the term of this patent is extended or adjusted under 35 U.S.C. 154(b) by 77 days.

(21) Appl. No.: 14/129,309

(22) PCT Filed: Jun. 27, 2012

(86) PCT No.: PCT/IL2012/050221
§ 371 (c)(1),
(2), (4) Date: Dec. 26, 2013

(87) PCT Pub. No.: WO2013/001534
PCT Pub. Date: Jan. 3, 2013

(65) Prior Publication Data
US 2014/0127824 A1    May 8, 2014

Related U.S. Application Data

(60) Provisional application No. 61/502,102, filed on Jun. 28, 2011.

(51) Int. Cl.
  *G01N 33/22* (2006.01)
  *A61N 1/40* (2006.01)
  *A61F 9/007* (2006.01)

(52) U.S. Cl.
  CPC .............. *G01N 33/227* (2013.01); *A61F 9/007* (2013.01); *A61N 1/403* (2013.01); *A61F 9/00718* (2013.01);
  (Continued)

(58) Field of Classification Search
  CPC ........................................... G01N 33/22

USPC .......... 436/107, 110–111, 117, 124, 135, 166, 436/169
See application file for complete search history.

(56) References Cited

U.S. PATENT DOCUMENTS 3,699,167 A * 10/1972 Kaiser ............................ 564/441
3,836,326 A *  9/1974 Sokol et al. ...................... 8/415
(Continued)

FOREIGN PATENT DOCUMENTS

EP        0611966    8/1994
WO    WO95/29394    11/1995
(Continued)

OTHER PUBLICATIONS

Holtorff, A. F. et al, Journal of Biological Chemistry 1940, 135, 377-392.*

(Continued)

*Primary Examiner* — Arlen Soderquist
(74) *Attorney, Agent, or Firm* — JMB Davis Ben-David

(57) ABSTRACT

A method for the detection of explosives using a single sample. The explosives include nitro aliphatic and nitro aromatic-based explosives. The method includes steps which require different pHs to discriminate between these types of explosives and at least in the detection step of the nitro aliphatic explosive requires the presence of a nitro aromatic compound. A kit for detecting explosives which includes a medium for collecting a sample, a base optionally impregnated on the medium; and a nitro aromatic solution for detecting a nitro aliphatic explosive by contacting the solution with the sample on the medium. A reagent including a nitro aromatic compound, having one or more additional electron withdrawing groups, in the presence of a basic compound usable for detecting nitro aliphatic explosives.

15 Claims, 2 Drawing Sheets

(52) U.S. Cl.
CPC ............... Y10T 436/170769 (2015.01); Y10T 436/173076 (2015.01); Y10T 436/173845 (2015.01); Y10T 436/178459 (2015.01); Y10T 436/19 (2015.01); Y10T 436/206664 (2015.01)

(56) References Cited

U.S. PATENT DOCUMENTS

| | | | | |
|---|---|---|---|---|
| 3,941,812 | A * | 3/1976 | Gilbert | 549/348 |
| 4,788,039 | A | 11/1988 | Glattstein | |
| 4,847,426 | A * | 7/1989 | Heck et al. | 568/587 |
| 4,857,070 | A * | 8/1989 | Seidel et al. | 8/408 |
| 5,032,291 | A * | 7/1991 | Sublette | A62D 3/37 210/757 |
| 5,117,002 | A * | 5/1992 | Buchanan et al. | 549/241 |
| 5,173,085 | A | 12/1992 | Brown et al. | |
| 5,296,380 | A | 3/1994 | Margalit | |
| 5,332,662 | A | 7/1994 | Ullman | |
| 5,376,556 | A * | 12/1994 | Tarcha et al. | 436/525 |
| 5,480,612 | A | 1/1996 | Margalit | |
| 5,531,845 | A * | 7/1996 | Flanigan et al. | 149/109.6 |
| 5,648,047 | A | 7/1997 | Kardish et al. | |
| 7,294,306 | B2 * | 11/2007 | Haas et al. | 422/411 |
| 7,410,612 | B1 | 8/2008 | Carrington | |
| 7,846,740 | B2 * | 12/2010 | Amisar | 436/164 |
| 7,939,029 | B2 * | 5/2011 | Eckels et al. | 422/401 |
| 8,969,095 | B1 * | 3/2015 | Haas | 436/164 |
| 8,999,722 | B2 * | 4/2015 | Swager et al. | 436/98 |
| 2002/0019558 | A1 * | 2/2002 | Okada et al. | 560/49 |
| 2003/0119069 | A1 * | 6/2003 | Schneider | G01N 27/44717 435/7.1 |
| 2004/0048329 | A1 | 3/2004 | Beuermann et al. | |
| 2007/0065944 | A1 * | 3/2007 | Nunes et al. | 436/8 |
| 2007/0202009 | A1 * | 8/2007 | Nunes et al. | 422/58 |
| 2008/0182334 | A1 | 7/2008 | Amisar | |
| 2009/0029480 | A1 | 1/2009 | Loane | |
| 2009/0043135 | A1 * | 2/2009 | Penzel | B01D 3/38 568/934 |
| 2009/0076307 | A1 * | 3/2009 | Uera et al. | 564/416 |
| 2009/0286322 | A1 | 11/2009 | Dancer | |
| 2011/0081723 | A1 * | 4/2011 | Miller et al. | 436/56 |
| 2012/0003746 | A1 * | 1/2012 | Amisar | 436/110 |

FOREIGN PATENT DOCUMENTS

| | | |
|---|---|---|
| WO | WO99/43846 | 9/1999 |
| WO | WO01/86289 | 11/2001 |
| WO | WO2005/089058 | 9/2005 |
| WO | WO2006/079167 | 8/2006 |
| WO | WO2009/027967 | 3/2009 |
| WO | WO2010/086834 | 8/2010 |

OTHER PUBLICATIONS

Hassall, C. H. et al, Analyst 1953, 78, 126-127.*
Jones, L. R. et al, Analytical Chemistry 1956, 28, 1493-1495.*
Urbanski, T., Bulletin de L'Academie Polonaise des Sciences Serie des Sciences Chimiques 1961, 9, 319-320.*
Ashworth, M. R. F. et al, Mikrochimica Acta 1967, 55, 358-365.*
Fyfe, C. A., Canadian Journal of Chemistry 1968, 46, 3047-3054.*
Gitis, S. S. et al, Russian Chemical Reviews 1978, 47, 1061-1083.*
Bartos, J. et al, Pure & Applied Chemistry 1979, 51, 1803-1814.*
Kawakami, T. et al, Tetrahedron Letters 1999, 40, 1157-1160.*
De Laat Joseph et al. "Catalytic decomposition of hydrogen peroxide by Fe III in homogeneous aqueous solution: Mechanism and kinetic modeling" Environmental Science and Technology, vol. 33, No. 16, Aug. 15, 1999, pp. 2726-2732.
E.Jungreiss et al. "Spot test for chlorate, bromate and iodate in admixtuer" Talanta, vol. 11, No. 4, Apr. 1, 1964, pp. 718-719.
T.F.A. Kiss: "Die durch Blei (II) und Kupfer (II) katalysierte Zersetzung von Wasserstoffperoxid als Endpunktindikation chelatometrischer Titrationen" Microchimica Acta, vol. 60, No. 3, May 1, 1972, pp. 420-423.
J.K. Kochi: "The decomposition of peroxides catalyzed by copper compounds and the oxidation of alkyl radicals by cupric salts" Journal of the American Chemical Society, vol. 85, No. 13, Jul. 5, 1963, pp. 1958-1968.
National Center for Forensic Science, "Training Guide for Explosive Analysis Training", Sep. 8, 2003, p. 1-25 (online), document retrieved on Jul. 28, 2010 (retrieved from http://www.ncfs.uct.cdu/twgfcx/docs/ExplosivcAnalystTrainingGuidc.pdf).
Toal et al., "Polymer sensors for nitroaromatic explosive detection", Apr. 27, 2006; Journal of Materials Chemistry, vol. 16, p. 2871-2883.
W.J. Williams, Handbook on Anion Determination,1982, pp. 259 &284.
Wolscy, "Pcrchloratc Tcsting in Chcmical Apparatus and Hoods", (1974); Journal of Chemical Education, vol. 51, No. 5, pp. A289 and A291.

* cited by examiner

REAGENT, METHOD AND KIT FOR THE DETECTION OF NITRO ALIPHATIC COMPOUNDS

CROSS-REFERENCE TO RELATED APPLICATION

This is the U.S. National Stage of International Application No. PCT/IL2012/050221, filed Jun. 27, 2012, which was published in English under PCT Article 21(2), which in turn claims the benefit of priority from U.S. Provisional Application Ser. No. 61/502102, filed Jun. 28, 2011, titled "Reagent, Method and Kit for the Detection of Nitro Aliphatic Compounds", incorporated herein by reference in its entirety.

FIELD OF THE INVENTION

The present invention relates to a reagent, a method and a kit for detecting explosives, including explosives containing nitro aliphatic compounds.

BACKGROUND OF THE INVENTION

The present invention relates to an improved reagent, method and kit for detecting explosives selected from nitro aliphatic compounds such as nitro methane, nitro ethane, and nitro propane.

The use of home-made, improvised explosives has been growing rapidly recently, and these improvised explosives include nitro aliphatic-based explosives, like nitro methane. These nitro aliphatic compounds are readily available in the market and easily converted to form an explosive mixture as strong as the standard explosives used today.

Methods and test kits for detecting explosives selected from nitro aromatics, organic nitrates, nitramines, inorganic nitrates, chlorates and bromates, have been described by Margalit in U.S. Pat. Nos. 5,296,380 and 5,480,612. Neither of these patents, however, describes detection of nitro aliphatic-based explosives.

SUMMARY OF THE INVENTION

It is an object of the present invention to enable the detection of explosive substances containing inter alia nitro aliphatic, nitro aromatic, organic peroxide, chlorate and/or bromate containing compounds.

It is a further object of the invention to provide for the sequential detection of nitro aliphatic, nitro aromatic, nitro amine, and nitro ester compounds, and inorganic nitrates, in the same sample.

A further object of the invention to provide for the sequential detection of nitro aliphatic, nitro aromatic, chlorate, bromate and peroxide compounds in the same sample.

Another object of the invention is to provide a novel reagent and method for detecting the presence inter alia of nitro amine and/or nitro ester explosive substances after nitro aliphatic compounds have been treated with base.

Other objects of the invention will be apparent to the reader from the description which follows.

In a first aspect of the present invention there is provided a method for the detection of explosive substances using a single sample. The method includes the steps of: providing a sample on a collection medium; contacting the sample with a nitro aromatic compound in a basic environment with a pH lower then the pH at which the Meisenheimer complex of the nitro aromatic compound is formed so as to detect the presence of a suspect nitro aliphatic explosive compound; if a color change occurs, comparing the color produced to a color chart to ascertain whether a nitro aliphatic explosive is present; if no color change has occurred, contacting the same sample with a basic compound so as to detect the presence of a suspect nitro aromatic explosive compound where the basic compound has a pH higher than 12; and if a color change occurs, comparing the color produced to a color chart to ascertain whether a nitro aromatic explosive is present.

In one embodiment of the method, the method further comprises the steps of: if no color change has occurred in the two previous contacting steps of the method, applying a Griess reagent to the same sample, to detect nitro ester and nitro amine explosive substances; if a color change occurs, comparing the color produced to a color chart to ascertain whether a nitro amine or a nitro ester explosive substance is present; if the color chart indicates the absence of nitro amine and nitro ester substances, contacting the same sample with a reducing metal powder suspension to indicate if a nitrate-based explosive is present; and if a color change occurs, comparing the color produced to a color chart to ascertain whether a nitrate-based explosive substance is present.

In another embodiment of the method, the method further comprises the steps of: if no color change has occurred in the two previous contacting steps of the method indicating the absence of nitro aliphatic and/or nitro aromatic explosive substances, applying an aromatic amine in a strongly acidic solution to the same sample, to detect if a chlorate or bromate explosive substance is present; if a color change occurs, comparing the color produced to a color chart to ascertain whether a chlorate or bromate explosive substance is present; if the color chart indicates the absence of a chlorate or bromate substance, contacting the same sample with a solution of transition metal cations to indicate if a peroxide explosive is present; and if a color change occurs, comparing the color produced to a color chart to ascertain whether a peroxide explosive substance is present. The embodiment may be further characterized by one or more of the following features: (a) the strong acid of the strongly acidic solution comprises sulfuric acid; and (b) the transition metal cations are selected from cations of iron, copper, manganese, chromium, cobalt and ruthenium.

In yet another embodiment of the method, where in the absence of a positive coloration indicating the presence of nitro aliphatic or nitro aromatic explosive substances, the method further includes the steps of providing a second sample of the suspect substance, and a step of testing for one or more compounds selected from chorates, bromates, peroxides, nitro amines, nitro esters and nitrates. In this embodiment, the step of testing further comprises the steps of: selecting one pair of the following pairs of steps and performing one or more steps of the pair selected: (a) contacting the second sample with a Greiss reagent, and if nitro esters or nitro amines are present a distinctive color change will be visible; and applying a metal powder suspension to the second sample, and if nitrates are present a distinctive color change will be visible; and (b) contacting the second sample with a strongly acidic solution of an aromatic amine and if chlorates and bromates are present a distinctive color change will be visible; and placing a drop of transition metal cations on the second sample, and if peroxides are present, a distinctive color change will be visible.

In yet another aspect of the invention, there is provided a method for the detection of explosive substances using a single sample. The method includes the steps of: providing a sample on a collection medium; contacting the sample with a nitro aromatic compound in a basic environment with a pH higher than 12 so as to detect the presence of a nitro aliphatic compound and/or a nitro aromatic compound in a suspect substance; and if a color change occurs, comparing the color produced to a color chart to ascertain whether a nitro aliphatic and/or a nitro aromatic compound is present.

In another aspect of the present invention there is provided a kit for use in colorimetric detection of explosive substances in a suspect sample. The kit includes: a collection medium for collecting a sample of the suspect substance; a reagent which is a solution of a nitro aromatic compound for detecting a nitro aliphatic explosive substance by contacting the nitro aromatic solution with a sample collected on the collection medium; and a basic compound.

In some embodiments of the kit, the basic compound is optionally impregnated on the collection medium.

In other embodiments of the kit, the kit further includes: a reagent which is a strongly acidic solution of one or more primary, secondary or tertiary aromatic amines for detecting chlorate or and bromate explosives; and a solution comprising cations of one or more transition metals for detecting peroxide-based explosives when no color change is observed after using the nitro aromatic and acidified amine reagents. In this embodiment, the reagents used are applied sequentially to a single sample. Also in this embodiment, the kit is further characterized by one or more of the following features: (i) the acidified amine reagent is dissolved in one or more water-miscible non-aqueous solvents; (ii) the one or more transition metals are selected from iron, copper, manganese, chromium, cobalt and ruthenium; (iii) the nitro aromatic reagent includes a highly basic substance; and (iv) the nitro aromatic reagent is applied on a basic substance.

In another embodiment of the kit, the basic compound is a strong base having a pH greater than the pH at which a Meisenheimer complex forms from the nitro aromatic explosive compound to be detected. The base here includes one or more basic materials selected from the group consisting of alkali hydroxides, alkali carbonates, alkali phosphates and tetra alkyl ammonium hydroxides.

In another embodiment of the kit, the kit further includes: a Greiss reagent for detecting nitro amine or nitro ester explosive substances; and a metal powder suspension for detecting nitrate-based explosive substances. In this embodiment, the reagents used are applied sequentially to a single sample.

In the kit, the nitro aromatic compound is dissolved in a DMSO-based solution with a w/w concentration of 0.01-5%.

In another aspect of the present invention, there is provided a reagent for the colorimetric detection of explosive materials containing nitro aliphatic compounds the nitro aromatic compound having one or more additional electron withdrawing groups in a basic environment. The nitro aromatic compound is in a basic environment where the basic environment has a pH below the pH at which a Meisenheimer complex is formed from the nitro aromatic compound. The basic environment includes a compound selected from a group consisting of alkali carbonates, alkali acetates, and alkali phosphates. The basic compound may be impregnated on a collection medium to which the nitro aromatic compound is contacted. The basic environment may be a base in the solid state. The pH of the basic environment is below pH 12.

The nitro aromatic compound is selected from the group of compounds comprising dinitrobenzaldehyde, dinitronapthalene, 2,4-dinitrotoluene, 2,4-dinitroanisol, 2,4-dinitrochlorobenzene, dinitrobenzene, and dinitrotrifluorotoluene.

In an embodiment of the reagent, the one or more nitro aromatic compounds is selected from a nitro aromatic compound having at least two nitro groups on an aromatic moiety.

In the reagent aspect of the invention, the nitro aromatic compound is dissolved in a non-aqueous water soluble solvent. The non-aqueous water soluble solvent may be at least partially water soluble.

In the reagent aspect of the invention, the nitro aromatic compound is in a basic environment at a pH higher than 12, the basic environment suitable for the simultaneous detection of nitro aromatic and nitro aliphatic- based explosives.

The nitro aromatic compound of the reagent is a compound which at a sufficiently high pH forms a colored Meisenheimer complex which has a substantially different color than the color produced by the reaction of the nitro aromatic compound with a nitro aliphatic explosive compound or the color produced by a nitro aromatic explosive compound at the same pH.

The various aspects of the present invention may be partially condensed, recapitulated and summarized as:

A. a reagent for detecting an explosive substance containing nitro aliphatic compounds;

B. a method for detecting an explosive substance which contains a nitro aliphatic compound selected from the group of nitro methane, nitro ethane and nitro propane, while using the same sample to sequententially detect an oxidant selected from chlorate, bromate, organic peroxides and nitrates;

C. a test kit for use in detecting an explosive substance which contains a nitro aliphatic compound selected from the group of nitro methane, nitro ethane and nitro propane, and one or more oxidants selected from chlorates, bromates, organic peroxides and nitrates. The kit inter alia comprises the following components: a solution of a nitro aromatic compound and a strongly acidic solution of one or more primary, secondary or tertiary aromatic amines and, optionally, the kit may include a solution of cations;

D. a method for detecting an explosive substance which contains a nitro aliphatic compound and at least one additional group of explosives selected from nitro aromatic compounds, nitro esters, nitro amines, inorganic nitrates, chlorates, bromates and peroxides; and E. a reagent kit for detecting an explosive substance which may contain nitro aliphatic compounds. The kit includes a solution comprising a nitro aromatic compound, together with a flow chart for use in detection of the explosive.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only. The drawings are presented in the cause of providing what is believed to be the most useful and readily understood description of the principles and conceptual aspects of the invention. In this regard, no attempt is made to show details of the invention in greater detail than is necessary for a fundamental understanding of the invention. The description taken with the drawings makes apparent to those skilled in the art how the invention may be embodied in practice.

DETAILED DESCRIPTION OF THE INVENTION

Figure 1A:
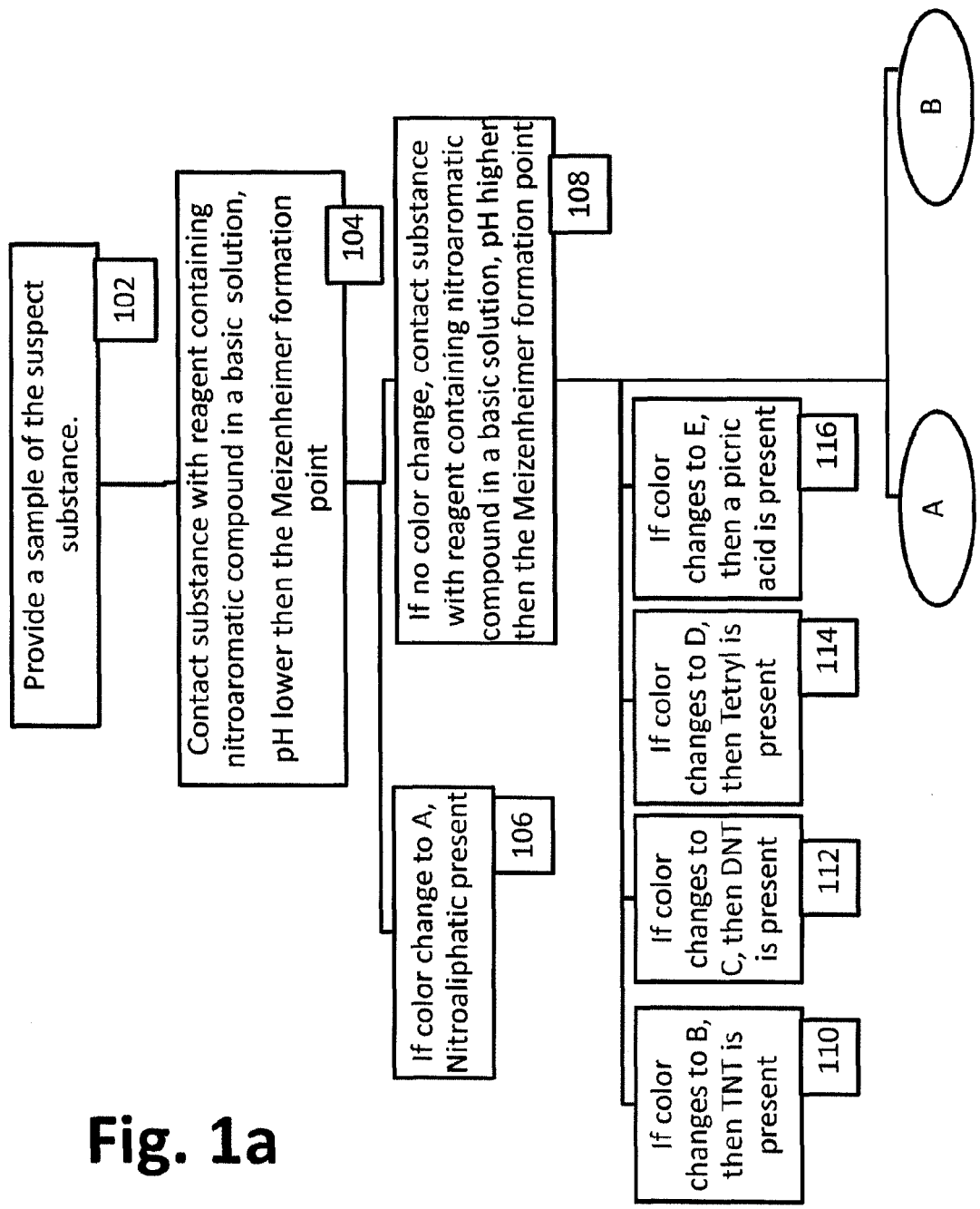
FIGS. 1A and 1B show a flowchart of the method of the present invention.

A method, kit and reagent for detecting nitro aliphatic compounds is here being provided.

Nitro aromatic compounds in a basic environment have been found to react with nitro aliphatic compounds to give a colored adduct. The nitro aromatic compound reacts with the alpha-carbon of the nitro aliphatic compound, the alpha-carbon having an activated hydrogen-carbon bond. Additionally, to better enable field detection of suspected nitro aliphatic explosives and to reduce the possibility of corrosion resulting from the required basic environment, the basic environment used with nitro aromatic compounds may be at much lower pHs than that of typical sodium hydroxide solutions (usually ~13). The base may even be provided in a solid state. Under these conditions, the reagent produces many fewer false positives than when higher pHs are used. Working at a lower pH reduces false positives because at pHs lower than 13, the number of materials that react with the nitro aromatic reagent is reduced making the test more specific.

It was further found that the color intensity and stability are enhanced when the nitro aromatic reagent is dissolved in non-aqueous solvents such as dimethyl sulfoxide (DMSO) and acetone.

Some nitro aromatic compounds themselves change color at higher pHs. However, when a nitro aromatic detection solution is kept at a lower basic pH (7<pH<12) and reacts with a nitro aliphatic compound, a substantially different color results from the one resulting when nitro aromatic and nitro aliphatic compounds react at higher pHs.

Nitro aromatic compounds in strongly basic solutions (>12) produce colored Meisenheimer complexes or adducts. However, when using these nitro aromatic compounds at basic pHs lower than the pH required for the formation of a nitro aromatic compound's associated Meisenheimer complex, the colors resulting from a reaction between the nitro aromatic and any nitro aliphatic compounds are easily discernible from the color of the associated Meisenheimer complex.

Typical changes in color of several nitro aromatic detecting reagents which react with nitro aliphatic compounds are shown below in Table I. Their Meisenheimer complex color is also shown in the middle column.

TABLE I

| Detecting Reagent A Nitro aromatic compound | Detecting Reagent Alone at a pH 13 | Reaction of Active Ingredient with Nitropropane |
| --- | --- | --- |
| 2,4 Dinitrobenzaldehyde | red | violet |
| 1,3 Dinitronaphtalene | red | red |
| DNT | green | light violet |
| TNT | brown | red-brown |
| Dinitrobenzotrifluoride | fuchsia | purple |
| Dinitrobenzene | brown -red | brown -red |

In a test kit of the invention, the kit includes:

(a) at least one of the reagents, preferably the first and second reagents, contains a nitro aromatic compound in at least one water-miscible non-aqueous solvent, such as at least one solvent selected from the group consisting of dimethyl sulfoxide (DMSO), dimethylformamide (DMF), dimethylacetamide, hexamethylphosphoramide, N-methylpyrrolidone, acetone and water-miscible alcohols and ethers. The first reagent is a nitro aromatic reagent which is used to react with a nitro aliphatic compound at a pH lower than the pH at which the Meisenheimer complex of the nitro aromatic detecting reagent is formed. The second reagent may be a basic compound with a pH greater than the pH at which a Meisenheimer complex is formed from the nitro aromatic explosive compound to be detected. Nitro aromatic explosive compounds react with highly basic compounds producing a distinctive color change.

In some kits only one reagent will be present. This reagent will be a basic nitro aromatic solution with a pH higher than the pH at which a Meisenheimer complex of the nitro aromatic reagent is formed. This strong base may be provided to a suspect nitro aromatic explosive substance in the solid state as well as in solution or as a collection paper impregnated with a strong base. This single reagent will allow simultaneous detection of both nitro aliphatic and nitro aromatic compounds.

The kit may also include one or more of the following reagents:

(b) at least one primary, secondary or tertiary aromatic amine preferably a secondary aromatic amine, such as a diarylamine, for example, the carbocyclic secondary aromatic amine, diphenylamine, for detecting chlorate and bromate containing explosives.

While use of secondary or tertiary aromatic amines, and in particular, diphenylamine, is presently preferred because they are significantly less toxic than primary amines and more sensitive for present purposes than aniline, nevertheless, use of a primary amine such as aniline is also deemed within the scope of the present invention; and/or (c) a strong acid preferably comprising sulfuric acid; and/or (d) at least one transition metal solution selected from iron ($Fe^{+3}$), copper, manganese, chromium, cobalt and ruthenium for detecting organic peroxides; and/or (e) in the absence of a positive coloration indicating the presence of nitro aliphatic, nitro aromatic, chlorate, bromate, or peroxide moieties, the method includes the possibility of providing a second sample of said suspect substance, and testing it with any reagent that can detect further groups of explosive substances selected from organic nitrates, nitro amines, nitro esters and urea nitrates. Typical reagents that may be included are (i) a suspension of an active metal powder, such as zinc powder, for detecting nitrates working in conjunction with (ii) a Greiss reagent for detecting nitro amines and nitro esters. The kit preferably includes at least one reagent adapted for testing for the presence of at least one of these latter explosive types.

In addition, the test kit of the invention preferably comprises at least one integral and/or discrete device for dispensing reagents, such as a spray or a dropping device.

Further, the test kit of the invention preferably comprises an absorbent collection medium, such as absorbent paper, for sampling a suspected explosive source wherein said suspected source includes a substance, a surface of an inanimate object and an exterior of a human. The absorbent media can be impregnated with a basic compound such as sodium carbonate, sodium phosphate, etc.

It will be appreciated that the reagent kit according to the invention may also include the above-described preferred features, so far as may be desired or appropriate.

In a presently preferred embodiment of the kit of the invention, each of the reagents are separately contained in closed plastic dropper bottles adapted for dispensing their contents in a drop wise manner. Also in a particular embodiment, every dropper bottle and its associated cap is identified by a color different from every other dropper bottle and its cap, thus enabling the user to match the correct bottle and cap.

The first reagent used in the method described below, is a basic nitro aromatic reagent for determining nitro aliphatic-based explosives. The second reagent is a highly basic environment that may be a solution or a solid, for the detection of nitro aromatic-based explosive compounds via the formation of a Meisenheimer complex. The first reagent is used at a basic pH lower than the pH at which its Meisenheimer complex forms that is generally lower than pH 12, while the second detecting reagent is at a pH in excess of that value, usually in excess of 13.

Generally, the nitro compound is a nitro aromatic compound containing at least one additional electron withdrawing group. However, often the nitro aromatic compound is one with at least two nitro groups positioned on the aromatic ring. Often, but without intending to limit the invention, the nitro groups are at the ring's 1, 3 positions.

In an embodiment of the present invention, preparation of the test reagents may be carried out as follows.

Reagent A (for Detecting Nitro Aliphatic Compounds)

A 0.1% w/v solution of dinitrobenzaldehyde in dimethyl sulfoxide (DMSO). The dinitrobenzaldehyde is preferably the 2,4-dinitrobenzaldehyde but the 3,5-dinitrobenzaldehyde may also be used.

Other nitro aromatic compounds that may be used in formulating reagent A in addition to dinitrobenzaldehyde include, but are not limited to, 3,5-dinitrobenztrifluoride and 1,3-dinitronapthalene. But these should not be considered as limiting the invention. Generally, the nitro aromatic compound used has at least one nitro group and at least one other electron withdrawing group on the aromatic moiety.

In addition to using DMSO as a solvent, the dinitrobenzaldehyde or other nitro aromatic compound used may be dissolved in other water miscible solvents such as, but without intending to limit the invention, acetone, isopropanol, and dimethyl ether.

Reagent B (for Detecting Chlorates or Bromates)

A liquid mixture is first prepared by carefully adding 95% sulfuric acid (400 ml) to a mixture of DMSO (90 ml), ethanol (100 ml) and water (500 ml). Diphenylamine (11 g) is then added to the liquid mixture while stirring, until a homogeneous solution is obtained. The reagent thus prepared is poured into a storage vessel prior to being used for filling ampoules. The solution is very stable under exposure to light and normal conditions; the ampoules do not need to be colored.

This reagent gives a deep blue coloration with chlorates or bromates within 1-2 seconds, which fades on standing. It is sensitive to as little as 0.0000001 $g/mm^2$ of chlorate or bromate. Perchlorate does not give a positive reaction with reagent B.

Reagent C (for Detecting Organic Peroxide)

A solution of 1% w/w $FeCl_3$ in dipropyleneglycol dimethyl ether. Solutions with cations of copper, manganese, chromium, cobalt and ruthenium may also be used.

Reagent D (For Detecting Nitro Amines and Nitro Esters)

A typical, but non-limiting, Griess reagent which can be used contains 0.2% napthylenediamine dihydrochloride and 2% sulphanilamide in 5% phosphoric acid.

Reagent E (for Detecting Nitrates)

A suspension of zinc dust in an organic solvent like isopropyl alcohol and/or isobutanol and which may also contain a silica-based suspension aid.

It should readily be understood by persons skilled in the art that other powdered metals may be used if their electrochemical properties are suitable. However, zinc dust is a preferred powdered metal which can easily reduce nitrates to nitrites.

Method

Figure 1B:
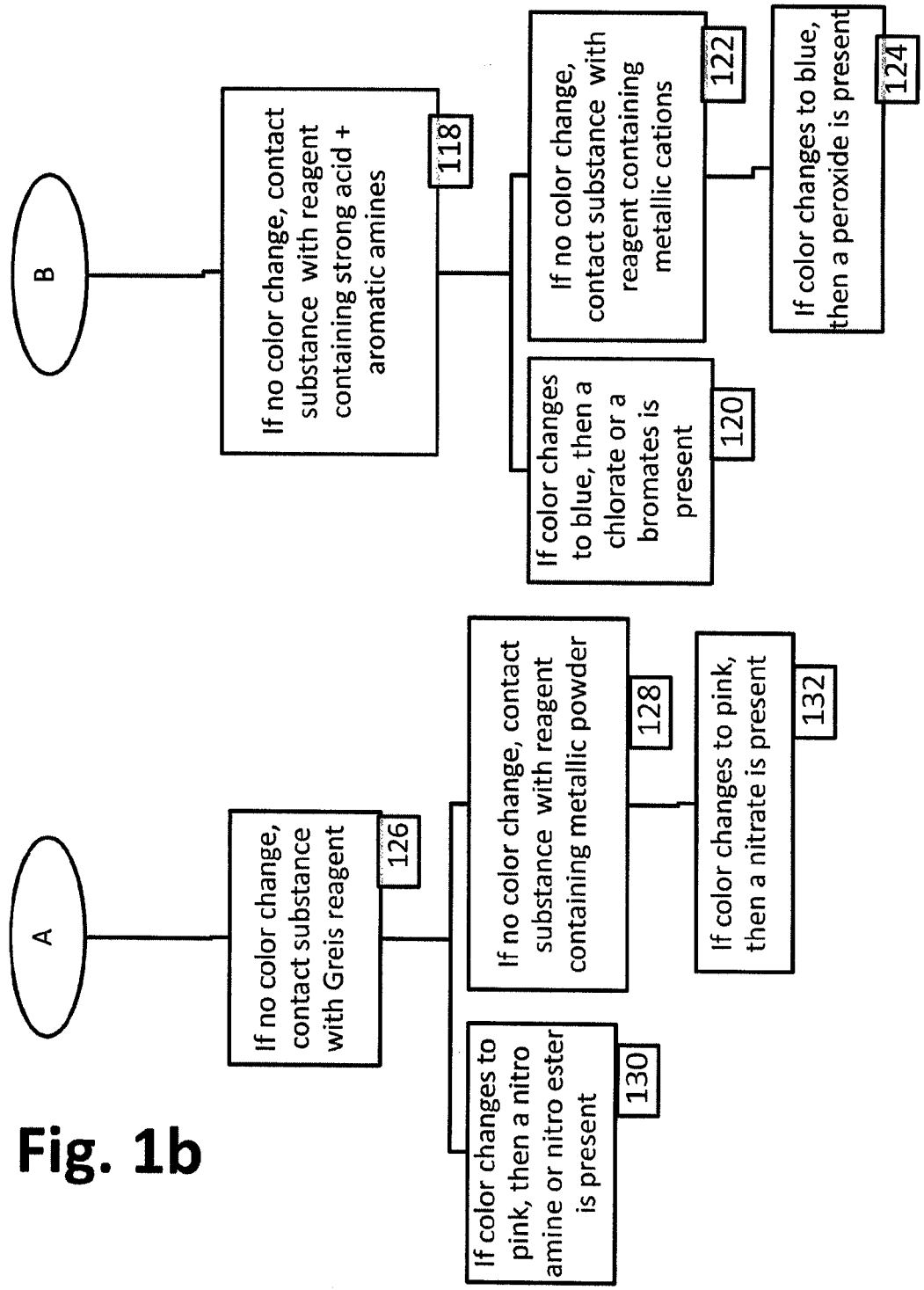

Numerals appearing below relate to the method shown in FIGS. 1A and 1B, to which reference is now made.

A sample of the suspect substance is provided on a collection medium (102). A drop of reagent A is contacted (104) with the collecting medium impregnated with sodium carbonate, for example, a filter paper, a polyethylene laminated paper, or one of these printed with a tacky layer of acrylate glue to enhance collection of suspect particles. Since the pH of the base used is less than the pH at which a Meisenheimer complex can form, the presence of a nitro aliphatic compound is indicated by the reagent changing from colorless to purple (106). The exact color produced upon reaction of reagent A with a nitro aliphatic compound depends on the nitro aromatic compound used in reagent A. See for example Table I above.

In the absence of any color change, a Meisenheimer reagent (a highly basic compound, that is usually at a pH>13) is placed on the same collection medium used previously (108). While the Meisenheimer complex of the reagent is colored, the presence of a nitro aromatic explosive substance will exhibit a color different from the color of the Meisenheimer complex. It has been noted that the detecting Meisenheimer complex does not mask a color change resulting from the presence of a nitro aromatic explosive substance.

The Meisenheimer complex may be made by adding a strong base to the nitro aromatic compound in reagent A. Adding the strong base brings the pH to above the pH at which its Meisenheimer complex forms, usually, a pH of 13 or higher. Generally, the nitro aromatic detecting compound used is a nitro aromatic containing at least one additional electron withdrawing groups. The nitro aromatic compound in reagent A used to detect nitro aliphatic-based explosives should be a different nitro aromatic compound from the suspect nitro aromatic-based explosive.

The presence of nitro aromatic-based explosives is detected by the formation of a Meisenheimer complex in a high pH solution which is contacted with the same sample used previously. An explosive substance is indicated, for example, by a purple color for trinitrotoluene (TNT) (110), a green color for dinitrotoluene (DNT) (112), a yellow color for picric acid (116), and an orange color for Tetryl, N-methyl-N, 2,4,6-tetranitroaniline(2,4,6-trinitrophenylmethylnitramine) (114), etc.

In the absence of any color change with reagent A, reagent B is contacted (118) with the same collection medium used previously. The presence of chlorates or bromates (120) is indicated by a color change typically the formation of a deep blue color. In the absence of a color change, a drop of reagent C, a solution of transition metal cations, is contacted with the same paper (122). Development of a blue color at this stage indicates the presence of a peroxide in the original sample (124).

In the absence or appearance of color after step 108, a drop of reagent D, a Griess reagent, may be contacted (126) with the same collection medium. The appearance of a pink-red color at this stage (130) indicates the presence of nitro esters or nitro amines in the original sample. In the absence of a color change, a drop of reagent E (zinc dust suspension) is contacted (128) with the same collection medium. Development of a color at this stage indicates the presence of a nitrate compound (132).

In the above described method, it should be understood that a color chart will usually be consulted after a color change because of the large number of colors and there various shades produced by the various reagents.

It should be noted that the above described method and collection of reagents provide improved detection capability, by using only one sample for all of the group's tests which are carried out sequentially. By use of "only one sample" the following is intended. All the steps through block 116 are carried out on a single sample. Then either the Greiss reagent branch of the flowchart beginning at block 126 or the amine reagent branch of the flowchart beginning at block 118 may be applied to the same sample. The two branches of the flowchart beginning with blocks 126 and 118 can not be carried out on a single sample. The flowchart must be viewed as a single sample flowchart from blocks 102 through 132 or from blocks 102 through 124. The testing of the second branch would then require a second sample.

Alternatively a new collection paper touched to a suspect substance or surface can be used at any stage. However, it should readily be understood that using a plurality of samples reduces the amount of substance to be detected with each successive sample and therefore reduces the likelihood of a successful test. Therefore a single sample on a single collection medium is preferred.

It should readily be understood by one skilled in the art that in the multi-step methods presented hereinabove, the method may be truncated once a reagent produces a color reaction without carrying out the remaining steps. This effectively allows the step employing the reagent producing the color change and all reagents employed in previous steps without producing a color change to be considered to be methods in themselves.

Surprisingly, the invention includes using a nitro aromatic compound solution for detecting other nitro aromatic or nitro aliphatic compounds that include potential explosives. A person skilled in the art, would have thought that the use of a nitro aromatic reagent for the detection of suspect nitro aromatic-based or nitro aliphatic-based explosives would be impossible as the color of the detecting nitro aromatic reagent itself would interfere with the detection of other nitro aromatic (or nitro aliphatic) explosive compounds. It would have been expected that the nitro aromatic compound used for detection would mask the normal color change of the suspect nitro aromatic explosive. However, what has been found is that under the conditions of the invention, no camouflaging of the color change occurs and the color produced is different between different nitro aromatics and nitro aliphatics, allowing for discrimination between them.

Examples demonstrating the invention discussed herein are indicated below:

1. A drop of 0.1% solution of 1,3-dinitronaphthalene in DMSO was placed on an absorbent paper with a drop of 0.1 M NaOH water solution. An immediate red color was produced. When exposed to nitro methane residues, the color slightly intensified but did not allow for any clear indication of a reaction.
2. A drop of a 0.1% solution of 1,3-dinitronaphthalene in DMSO was placed on an absorbent paper impregnated with sodium carbonate (10 gr per square meter). No color change was observed. When exposed to nitro methane residues, a strong red color was immediately produced with a clear indication of a reaction.
3. A drop of 0.1% solution of 2,4-dinitrobenzaldehyde in DMSO was placed on an absorbent paper with a drop of 0.1 M NaOH water solution. An immediate red color was produced. When exposed to nitro methane residues, a purple color was immediately produced with a clear indication of a reaction.
4. A drop of 0.1% solution of 2,4-dinitrobenzaldehyde in DMSO was placed on an absorbent paper impregnated with sodium carbonate, (10 gr per square meter). No color change was observed. When exposed to nitro methane residues, a strong red color was immediately produced with a clear indication of a reaction.
5. Tests were done with other nitro compounds with similar results. The same tests were repeated with acetone and other polar solvents with similar results
6. Tests were done replacing sodium carbonate with sodium acetate, sodium phosphates, cesium carbonate and they all gave results similar to the ones described above.

While particular embodiments of the invention have been described hereinabove, it will be appreciated that the present invention is not limited thereto, since as will be readily apparent to persons skilled in the art, many modifications or variations can be made.

It is to be appreciated that certain features of the invention, which are, for clarity, described in the context of separate embodiments, may also be provided in combination in a single embodiment. Conversely, various features of the invention, which are, for brevity, described in the context of a single embodiment, may also be provided in any suitable sub-combination or combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention. Therefore, it will be appreciated by persons skilled in the art that the present invention is not limited by what has been particularly shown and described herein above. Rather, the scope of the invention is defined by the claims that follow.

The invention claimed is:

1. A method for the detection of explosive substances using a single sample, the method comprising the steps of:
   providing a sample on a collection medium;
   contacting the sample with a nitro aromatic compound in a basic environment with a pH lower then the pH at which the Meisenheimer complex of the nitro aromatic compound is formed so as to detect the presence of a suspect nitro aliphatic explosive compound;
   if a color change occurs, comparing the color produced to a color chart to ascertain whether a nitro aliphatic explosive is present;
   if no color change has occurred, contacting the same sample with a basic compound so as to detect the presence of a suspect nitro aromatic explosive compound where said basic compound has a pH higher than 12; and
   if a color change occurs, comparing the color produced to a color chart to ascertain whether a nitro aromatic explosive is present.

2. A method according to claim 1, further comprising the following steps:
   If no color change has occurred in the two previous contacting steps of the method, applying a Griess reagent to the same sample, to detect nitro ester and nitro amine explosive substances;
   if a color change occurs, comparing the color produced to a color chart to ascertain whether a nitro amine or a nitro ester explosive substance is present;
   if the color chart indicates the absence of nitro amine and nitro ester substances, contacting the same sample with a reducing metal powder suspension to indicate if a nitrate explosive is present; and
   if a color change occurs, comparing the color produced to a color chart to ascertain whether a nitrate explosive substance is present.

3. A method according to claim 1 further comprising the following steps:
   If no color change has occurred in the two previous contacting steps of the method indicating the absence of nitro aliphatic and/or nitro aromatic explosive substances, applying an aromatic amine in a strongly acidic solution to the same sample to detect if a chlorate or bromate explosive substance is present;
   if a color change occurs, comparing the color produced to a color chart to ascertain whether a chlorate or bromate explosive substance is present;
   if the color chart indicates the absence of a chlorate or bromate substance, contacting the same sample with a solution of transition metal cations to indicate if a peroxide explosive is present; and
   if a color change occurs, comparing the color produced to a color chart to ascertain whether a peroxide explosive substance is present.

4. A method according to claim 3, which is further characterized by at least one of the following features:
   (a) the strong acid of said strongly acidic solution comprises sulfuric acid; and
   (b) said transition metal cations are selected from cations of iron, copper, manganese, chromium, cobalt and ruthenium.

5. A method according to claim 1 where in the absence of a positive coloration indicating the presence of a nitro aliphatic or nitro aromatic explosive substance, the method further comprises the step of providing a second sample of said suspect substance, and a step of testing for at least one compound selected from chorates, bromates, peroxides, nitro amines, nitro esters and nitrates.

6. A method according to claim 5, wherein said step of testing further comprises the steps of:
   selecting one pair of the following pairs of steps and performing at least one step of the pair selected:
   (a) contacting the second sample with a Greiss reagent and if nitro esters or nitro amines are present a distinctive color change will be visible; and applying a metal powder suspension to the second sample and if nitrates are present a distinctive color change will be visible; and
   (B) contacting the second sample with a strongly acidic solution of an aromatic amine and if chlorates and bromates are present a distinctive color change will be visible; and
   placing a drop of transition metal cations on the second sample and if peroxides are present, a distinctive color change will be visible.

7. A kit for use in colorimetric detection of explosive substances in a suspect sample, the kit comprising:
   a collection medium for collecting a sample of the suspect substance;
   a reagent which is a solution of a nitro aromatic compound for detecting a nitro aliphatic explosive substance by contacting the nitro aromatic solution with a sample collected on said collection medium; and
   a basic compound.

8. A kit according to claim 7 wherein said basic compound is optionally impregnated on said collection medium.

9. A kit according to claim 7 further comprising:
   a reagent which is a strongly acidic solution of at least one primary, secondary or tertiary aromatic amine for detecting chlorate- or and bromate-based explosives; and
   a solution comprising cations of at least one transition metal for detecting peroxide-based explosives when no color change is observed after using the nitro aromatic and acidified amine reagents.

10. A kit according to claim 9, which is further characterized by at least one of the following features:
    (i) said acidified amine reagent is dissolved in at least one water-miscible non-aqueous solvent;
    (ii) said at least one transition metal is selected from iron, copper, manganese, chromium, cobalt and ruthenium; and
    (iii) said nitro aromatic reagent includes a highly basic substance;
    (iv) said nitro aromatic reagent is applied on a basic substance.

11. A kit according to claim 9 further comprising:
    a Greiss reagent for detecting nitro amine or nitro ester explosive substances; and
    a metal powder suspension for detecting nitrate-based explosive substances.

12. A kit according to claim 7 wherein said basic compound is a strong base having a pH greater than the pH at which a Meisenheimer complex forms from a nitro aromatic explosive compound to be detected.

13. A kit according to claim 12, wherein said base includes at least one basic material selected from the group consisting of alkali hydroxides, alkali carbonates, alkali phosphates and tetra alkyl ammonium hydroxides.

14. A kit according to claim 7 further comprising:
    a Greiss reagent for detecting nitro amine or nitro ester explosive substances; and
    a metal powder suspension for detecting nitrate-based explosive substances.

15. A kit according to claim 7 were said nitro aromatic compound is dissolved in a DMSO solution with a w/w concentration of 0.01-5%.

* * * * *